US010870830B2

(12) United States Patent
Jo et al.

(10) Patent No.: US 10,870,830 B2
(45) Date of Patent: Dec. 22, 2020

(54) METHOD FOR CULTURING DIFFERENTIATION-PROMOTING AND -SUSTAINING SPHEROID FORM OF TONSIL-DERIVED STEM CELLS

(71) Applicants: EWHA UNIVERSITY—INDUSTRY COLLABORATION FOUNDATION, Seoul (KR); KOREA UNIVERSITY RESEARCH AND BUSINESS FOUNDATION, Seoul (KR)

(72) Inventors: Inho Jo, Cheonan-si (KR); Yoon Shin Park, Seoul (KR); Sang Hoon Lee, Seoul (KR); Ji-Young Hwang, Seoul (KR); Yesl Jun, Seoul (KR); Yoon Mi Jin, Seoul (KR); Gyung Ah Kim, Anyang-si (KR); Ha Yeong Kim, Seongnam-si (KR); Han Su Kim, Seoul (KR); Sung Chul Jung, Seoul (KR)

(73) Assignees: EWHA University—Industry Collaboration Foundation, Seoul (KR); Korea University Research and Business Foundation, Seoul (KR)

( * ) Notice: Subject to any disclaimer, the term of this patent is extended or adjusted under 35 U.S.C. 154(b) by 128 days.

(21) Appl. No.: 15/561,500

(22) PCT Filed: Mar. 23, 2016

(86) PCT No.: PCT/KR2016/002914
§ 371 (c)(1),
(2) Date: Sep. 25, 2017

(87) PCT Pub. No.: WO2016/153263
PCT Pub. Date: Sep. 29, 2016

(65) Prior Publication Data
US 2019/0194611 A1    Jun. 27, 2019

(30) Foreign Application Priority Data

Mar. 26, 2015   (KR) ................. 10-2015-0042774
Mar. 23, 2016   (KR) ................. 10-2016-0034484

(51) Int. Cl.
| | | |
|---|---|---|
| *C12N 5/071* | (2010.01) | |
| *C12N 5/074* | (2010.01) | |
| *C07K 14/635* | (2006.01) | |
| *C12N 5/0775* | (2010.01) | |
| *C12N 5/078* | (2010.01) | |

(52) U.S. Cl.
CPC .......... *C12N 5/0617* (2013.01); *C07K 14/635* (2013.01); *C12N 5/0651* (2013.01); *C12N 5/0668* (2013.01); *C12N 2501/16* (2013.01); *C12N 2501/41* (2013.01); *C12N 2506/1392* (2013.01); *C12N 2513/00* (2013.01); *C12N 2533/30* (2013.01); *C12N 2535/00* (2013.01)

(58) Field of Classification Search
None
See application file for complete search history.

(56) References Cited

U.S. PATENT DOCUMENTS

2009/0123433 A1   5/2009  Shroff
2015/0018750 A1   1/2015  Ueda et al.

FOREIGN PATENT DOCUMENTS

| KR | 10-1017710    | B1 |   | 2/2011  |
|----|---------------|----|---|---------|
| KR | 20130013537   | A  | * | 2/2013  |
| KR | 10-1282926    | B1 |   | 7/2013  |
| KR | 20130121606   | A  | * | 11/2013 |
| KR | 10-2014-0113139 | A |   | 9/2014  |
| KR | 10-2014-0130159 | A |   | 11/2014 |
| KR | 10-2014-0135263 | A |   | 11/2014 |
| KR | 10-1508413    | B1 |   | 4/2015  |
| KR | 10-1520531    | B1 |   | 5/2015  |

OTHER PUBLICATIONS

Rejnmark et al., "PTH replacement therapy of hypoparathyroidism", Osteoporosis International, vol. 24, pp. 1529-1536. (Year: 2013).*
Woods Ignatoski et al., "Differentiation of precursors into parathyroid-like cells for treatment of hypoparathyroidism", Surgery, vol. 148, pp. 1186-1190. (Year: 2010).*
Chou et al., "Treatment of osteoporosis with TheraCyte-encapsulated parathyroid cells: a study in a rat model", Osteoporosis International, vol. 17, pp. 936-941. (Year: 2006).*
Ingram et al., 'Spheroid cell culture on PDMS hydrophobic surfaces and integration into microfluidic devices', 15th International Conference on Miniaturized Systems for Chemistry and Life Sciences, WA, USA: 1539-1541 (2011).
International Search Report for PCT/KR2016/002914 (dated Nov. 18, 2016).
Embryoid body from Wikipedia website https://en.wikipedia.org/w/index.php?title=Embryoid_body&oldid=930612658 pp. 1-11.
Stem Cell Basics; V. What are the similarities and differences between embryonic and adult stem cells?; National nstitutes of Health website https://stemcells.nih.gov/info/basics/5.htm pp. 1-2.

* cited by examiner

*Primary Examiner* — Michelle F. Paguio Frising
(74) *Attorney, Agent, or Firm* — Melissa M. Hayworth; E. Joseph Gess (57) ABSTRACT

The present invention relates to a method for producing a spheroid form of tonsil-derived stem cells, the method enhances growth and differentiation efficiency of the tonsil-derived stem cells. The present method also produces a spheroid form of para-thyroid hormones. The method for producing a spheroid form of tonsil-derived stem cells enhances the proliferation rate of the stem cells per se and significantly increase differentiation potency into parathyroid cells.

11 Claims, 9 Drawing Sheets
Specification includes a Sequence Listing.

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Forward primer for parathyroid hormone

<400> SEQUENCE: 1
gagtagaatg gctgcgtaag aag                                           23

<210> SEQ ID NO 2
<211> LENGTH: 21
<212> TYPE: DNA
<213> ORGANISM: Artificial Sequence
<220> FEATURE:
<223> OTHER INFORMATION: Reverse primer for parathyroid hormone

<400> SEQUENCE: 2
ttcatggctc tcaaccaaga c                                             21

<210> SEQ ID NO 3
<211> LENGTH: 21
<212> TYPE: DNA
<213> ORGANISM: Artificial Sequence
<220> FEATURE:
<223> OTHER INFORMATION: Forward primer for GAPDH

<400> SEQUENCE: 3
ggagcgagat ccctccaaaa t                                             21

<210> SEQ ID NO 4
<211> LENGTH: 23
<212> TYPE: DNA
```

```
<213> ORGANISM: Artificial Sequence
<220> FEATURE:
<223> OTHER INFORMATION: Reverse primer for GAPDH

<400> SEQUENCE: 4
ggctgttgtc atacttctca tgg                                              23
```

METHOD FOR CULTURING DIFFERENTIATION-PROMOTING AND -SUSTAINING SPHEROID FORM OF TONSIL-DERIVED STEM CELLS

The present application is a National Stage Application under 35 U.S.C. § 371 of International Application No. PCT/KR2016/002914 filed Mar. 23, 2016, which claims the benefit of priority to Korean Patent Application No. 10-2015-0042774 filed Mar. 26, 2015, and Korean Patent Application No. 10-2016-0034484 filed Mar. 23, 2016, the disclosures of all of which are hereby incorporated by reference in their entireties. The International Application was published in Korean on Sep. 29, 2016 as WO 2016/153263.

FIELD OF THE INVENTION

The present invention relates to a method for producing a spheroid form of tonsil-derived stem cells and a method for differentiating the same into parathyroid cells.

BACKGROUND OF THE INVENTION

Stem cells, capable of being differentiated into various cells that make up living tissues, generally refer to undifferentiated cells in a previous stage of differentiation that can be obtained from each tissue of embryos, fetuses or adult cells. They are differentiated into specific types of cells by differentiation stimulus (environment), have the self-renewal property of producing cells identical to themselves by cell division, and have the plasticity of being differentiated into different cells according to differentiation stimulus.

Stem cells can be divided into pluripotent, multipotent and unipotent stem cells according to differentiation potency thereof. The pluriopotent stem cells are totipotent cells having the potential to be differentiated into all types of cells, while some of stem cells have the potential of multi-potency or unipotency.

There has been an active R&D effort on the development of cell therapy products based on the differentiation potency of the above-mentioned stems cells. However, the cell therapy products using embryo stem cells have caused ethnical issues or histocompatibility discrepancy ones and a use of dedifferentiated stem cells for cell therapy products has a potential problem of causing tumors.

Accordingly, there have been many researches on using mesenchymal stem cells (MSCs), which have been known to have low differentiation potency but to be relatively safe. The MSCs, which are multi-potential non-hematopoietic progenitor cells present in adult bone marrow, etc., refer to cells that can be differentiated into various types of cells such as fat, cartilage, bone, muscle and skin. There have been various clinical researches for regenerating tissues by using those MSCs, which have the possibility of being applied to an organ transplant field.

Out of the MSCs, however, some stem cells are difficult to use due to a remarkable limitation to obtaining those cells. For example, the MSCs derived from cord blood and fat tissues must be obtained by means of an invasive method. Cells, which can be obtained by means of the most non-invasive method, are MSCs collected from marrow. However, a bone marrow aspiration requires anesthesia and causes pains, such that there is a limitation to uses thereof. Alternatively, there is a demand for a cell-acquisition method, etc., using peripheral blood in order to separate patient-specific cells. In case of the peripheral blood, however, there is a too small number of MSCs that can be separated from adults and a separation method thereof is not economical. Even if MSCs are separated, in most cases the MSCs could not be proliferated enough to be used in cell therapy. Therefore, there is a need for developing an alternative measure with an enhanced practicability. Furthermore, adult stem cells obtained from old patients show a remarkable decline in proliferation ability in comparison with the cells obtained from young patients, and also have a less migration ability due to secretion of various factors and lesion of stem cells, such that there is a need for obtaining cells from tissues that can be naturally separated or left out from young patients. Also, such obtained cells need to be quantitatively secured enough for easy experiments and differentiation potency thereof needs to be maintained well at a time of subculture of cells.

Furthermore, most of the adult stem cells have good differentiation potency into mesoderm origin tissues, but cannot be easily differentiated into ectoderm and endoderm origin tissues, such that it is necessary to overcome such limited differentiation problem.

Meanwhile, parathyroid hormone (PTH) consists of 84 amino acids secreted from a parathyroid, serves as a key hormone to adjust an in vivo calcium concentration, and can be used as a therapeutic agent for hypoparathyroidism, osteoporosis and the like. Therefore, there is a growing demand for the parathyroid hormone, but a method for effectively producing the parathyroid hormone has not been developed yet. In particular, a parathyroid tissue, which is an endoderm origin tissue, is very difficult to be differentiated from the stem cells derived from adults, and a differentiation efficiency thereof is not enough to be used commercially too.

Accordingly, there is a need for conducting a research and development on how to secure stem cells and differentiated cells appropriate for acting on a human body by making attempts on a research and development on a method for optimally differentiating stem cells with a continuous and high differentiation efficiency.

PRIOR ART REFERENCES

Patent Documents

Korean Patent Publication No. 10-2014-0130159
Korean Patent Publication No. 10-2014-0135263
Korean Patent Registration No. 10-1282926

SUMMARY OF THE INVENTION

The present invention provides a method for producing a spheroid form of tonsil-derived stem cells, the method comprising:

(a) transferring a suspension of tonsil-derived stem cells into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension; and (b) producing a spheroid form of tonsil-derived stem cells by culturing the tonsil-derived stem cells prepared by the step (a) in the hemispherical microwell.

The present invention also provides a method for producing a spheroid form of parathyroid cells from tonsil-derived stem cells, the method comprising:

(a) transferring a suspension of tonsil-derived stem cells into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension;

(b) producing a spheroid form of tonsil-derived stem cells by culturing the tonsil-derived stem cells prepared by the step (a) in the hemispherical microwell; and (c) adding activin A and sonic hedgehog into the spheroid form of tonsil-derived stem cells of the step (b), thereby differentiating the stem cells into parathyroid cells.

The present invention also provides a method for producing parathyroid hormone, the method comprising:

(a) transferring a suspension of tonsil-derived stem cells into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension;

(b) producing a spheroid form of tonsil-derived stem cells by culturing the tonsil-derived stem cells prepared by the step (a) in the hemispherical microwell;

(c) adding activin A and sonic hedgehog into the spheroid form of tonsil-derived stem cells of the step (b), thereby differentiating the stem cells into parathyroid cells; and (d) separating parathyroid hormone from culture medium or cell lysis solution obtained from the step (c).

The present invention also provides a method for producing a spheroid form of parathyroid cells, the method comprising:

(a) treating tonsil-derived stem cells with activin A and sonic hedgehog to differentiate the tonsil-derived stem cells;

(b) transferring a suspension of cells of the step (a) into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension; and (c) adding activin A and sonic a hedgehog into the suspension of cells of the step (b) to differentiate the cells into a spheroid form of parathyroid cells.

The present invention also provides a method for producing parathyroid hormone, the method comprising:

(a) treating tonsil-derived stem cells with activin A and sonic hedgehog to differentiate the tonsil-derived stem cells;

(b) transferring a suspension of cells of the step (a) into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension;

(c) adding activin A and sonic a hedgehog into the suspension of cells of the step (b) to differentiate the cells into a spheroid form of parathyroid cells; and (d) separating parathyroid hormone from culture medium or cell lysis solution obtained from the step (c).

The present invention also provides a spheroid form of tonsil-derived stem cells produced by the method for the producing a spheroid form of tonsil-derived stem cells.

The present invention also provides a spheroid form of parathyroid cells produced by the method for producing a spheroid form of parathyroid cells.

The present invention also provides a pharmaceutical composition containing a spheroid form of tonsil-derived stem cells produced by the method for producing a spheroid form of tonsil-derived stem cells.

The present invention also provides a pharmaceutical composition for preventing or treating hypoparathyroidism or osteoporosis, containing a spheroid form of parathyroid cells produced by the method for producing a spheroid form of parathyroid cells.

While conducting a study on a method for culturing tonsil-derived stem cells with a continuous and high differentiation efficiency, the present inventors identified that the method showed a remarkable differentiation efficiency in such a way that tonsil-derived stem cells were cultured into a spheroid form of tonsil-derived stem cells, from which parathyroid cells were differentiated accordingly, thereby completing the present invention.

According to the present invention, tonsil-derived stem cells mean undifferentiated stem cells that have the ability to be differentiated into at least two new cells, while having the ability to replicate themselves derived from a tonsil, which is a tissue located inside a neck and at a back portion of a nose, such that the tonsil prevents our body from being invaded by substances such as germs from outside and serves as an lymphoepithelial immune tissue at the same time.

According to the present invention, parathyroid cells mean cells making up a parathyroid, which is an endocrine organ attached to a thyroid, such that the parathyroid cells secrete parathyroid hormone (PTH), and adjust a metabolism of calcium and phosphorus of body fluids. In the present invention, any cells may be included in parathyroid cells, as long as the cells secrete parathyroid hormone.

According to the present invention, a spheroid form or a spheroid shape means a stereostructure in which cells are condensed enough to be generally seen as a circular or an elliptical shape in cross-section, and should be judged, considering characteristics of cells or cell aggregates. According to the present invention, the spheroid form or the spheroid shape may not mean a completely globular form or a spheroid form.

The present invention provides a method for producing a spheroid form of tonsil-derived stem cells, the method comprising:

(a) transferring a suspension of tonsil-derived stem cells into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension; and (b) producing a spheroid form of tonsil-derived stem cells by culturing the tonsil-derived stem cells prepared by the step (a) in the hemispherical microwell.

In the method for producing a spheroid form of tonsil-derived stem cells according to the present invention, as a culture continues, a diameter of a cell aggregate is decreased and then kept at a certain level, such that rough shapes on a surface of the cell aggregate are gradually changed into such a relatively smooth state as to take a spheroid form of three-dimensional shape as mentioned in the present invention. The cell aggregate may have such a size that an activity of the cells inside the cell aggregate and a three-dimensional shape can be simultaneously maintained, for example, a diameter of the cell aggregate can amount to 250 μm or less, preferably 80 to 250 μm.

A spheroid form of tonsil-derived mesenchymal stem cells (MSCs) according to the present invention have a comparatively smooth outer surface because an intercellular junction boundary is small due to junctional complex and extracellular matrix (ECM) between neighbored cells.

The method for producing a spheroid form of tonsil-derived stem cells according to the present invention allows tonsil-derived stem cells to be cultured in a form of spheroid to thereby enhance a proliferation rate of the stem cells per se, and allows the same to increase a differentiation potency into various cells such as parathyroid cells to thereby have a remarkable effect on growth and differentiation of stem cells depending on culture of tonsil-derived stem cells. In other words, according to the present invention, a physical culture environment is set up as the hemispherical microwell, which is formed by means of the hardened liquid polymer, such that a proliferation rate of the tonsil-derived stem cells per se is increased, a period of using a differentiation-inducing agent is remarkably reduced at a time of cell differentiation, and also a pre-differentiation period in a two-dimensional aspect is omitted, thereby achieving an effect of reducing a use of a reagent and greatly contributing to economic effects, for example, reduction of labor costs and shortening of working hours.

The method for producing a spheroid form of tonsil-derived stem cells according to the present invention comprises: (a) transferring a suspension of tonsil-derived stem cells into a hemispherical microwell, which is formed in such a way that at least one liquid polymer is hardened in a form of hemispherical microwell, wherein the at least one liquid polymer is selected from polydimethylsiloxane, silicon polymer, polybutadiene, polyisobutylene or polyurethane, forming a meniscus due to surface tension.

The production of the hemispherical microwell used in the present invention is described in Korean Patent Registration No. 10-1282926 (producing a hemispherical microwell using surface tension and forming a cell aggregate using the same); the contents of which are hereby incorporated by reference.

The microwell for producing a spheroid form of tonsil-derived stem cells according to the present invention may be one that is included in a mold having a concave structure, which is used to form a spheroid form of cell aggregates at a time of culturing tonsil-derived stem cells.

The microwell can be manufactured in such a way that the liquid polymer is transferred thereinto by such a proper amount as to form a meniscus within the same due to surface tension and then is hardened by means of heat or UV, wherein the liquid polymer is transferred into the same by an amount appropriate to form the meniscus therein or fills up to a considerable part or more of the microwell, and then removed by means of the method for removing the liquid polymer.

Figure 1:
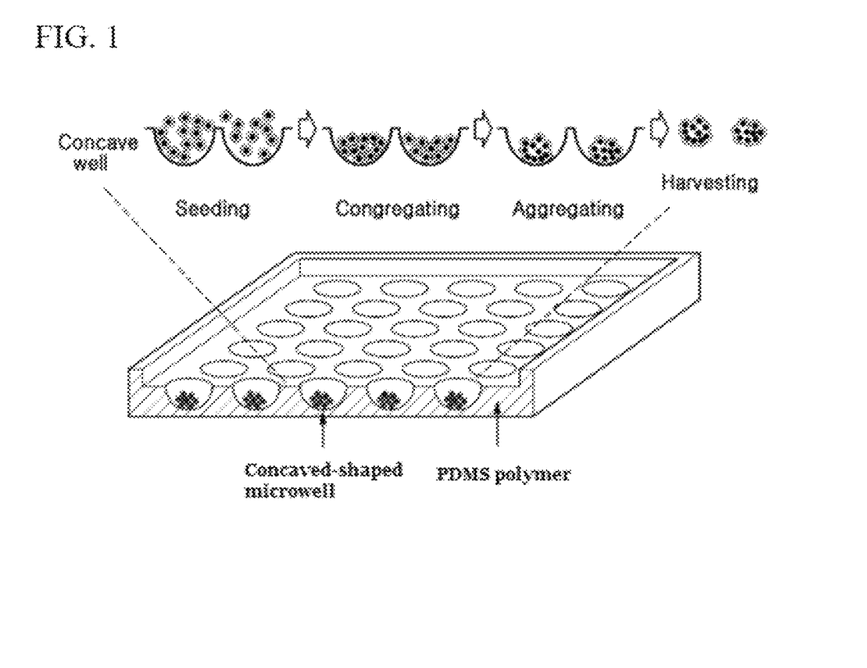
FIG. 1 depicts a diagram illustrating a process of producing a spheroid form of cells, using a multiple-concave mold that is formed in such a way that polydimethylsiloxane (PDMS) is hardened.

Preferably, the microwell has a concave structure, which is formed in such a way that a liquid polymer of polydimethylsiloxane (PDMS) is hardened, wherein several to thousands thereof may be included in one mold (a multiple-concave type mold). According to an embodiment of the present invention, a rough structure of the mold is shown in FIG. 1.

The microwell may be between 100 to 1000 μm width, e.g., between 300 to 600 μm width, and may be between 60 to 600 μm depth, e.g., between 200 to 400 μm depth.

The microwell may be preferably formed in such a way that at least one liquid polymer is hardened, wherein the at least one liquid polymer is selected from polydimethylsiloxane, silicon polymer, polybutadiene, polyisobutylene or polyurethane, more preferably polydimethylsiloxane. In other words, the liquid polymer forms a meniscus within the microwell due to surface tension, wherein the liquid polymer having formed the meniscus is hardened, to allow an appropriate environment for culturing tonsil-derived stem cells as spheroid-formed cells.

The microwell may be coated to prevent cells from being attached onto a hemispherical surface of the well before transferring cells therein, for example, by means of treatment, such as coating of the above-mentioned well for culturing a cell aggregate with bovine serum albumin.

In case of the above-mentioned suspension of tonsil-derived stem cells, cells may be included in one microwell (i.e., the number of cells per well) by up to $1 \times 10^2$ to $1 \times 10^5$ cells, preferably by up to $5.0 \times 10^2$ to $1 \times 10^4$ cells.

The suspension of tonsil-derived stem cells may contain a stem cell culture medium generally used in the art, preferably using DMEM-HG (Dulbecco's modified Eagle's medium-High Glucose) medium containing fetal bovine serum and antibiotics, wherein the antibiotics may be streptomycin, ampicillin, etc., but not particularly limited thereto.

The method for producing a spheroid form of tonsil-derived stem cells according to the present invention comprises: (b) producing a spheroid form of tonsil-derived stem cells by culturing the spheroid form of tonsil-derive stem cells of the step (a) in a hemispherical microwell. The step of culturing tonsil-derived stem cells may be performed by using the above-mentioned stem cell culture medium, preferably for 1 to 20 days, more preferably for 1 to 14 days, and especially more preferably for 2 to 7 days. These culture periods are preferable, but if the cells reach a desired size or shape, while a process of forming spheroid form of cells is taken into consideration, a desired spheroid form of cells can be produced by adjusting the culture periods.

The method for producing a spheroid form of tonsil-derived stem cells according to the present invention may further comprise a step of harvesting the produced spheroid form of tonsil-derived stem cells.

The step of harvesting a spheroid form of tonsil-derived stem cells is the process that harvests the spheroid form of tonsil-derived mesenchymal stem cells produced by means of the above-mentioned process. A size of the harvested spheroid form of tonsil-derived mesenchymal stem cells (a cell aggregate) can be adjusted by means of a method for adjusting a diameter and depth of the microwell, and a cell aggregate can be produced in a substantially uniform size.

For example, in case of producing a cell aggregate by using a microwell with an average diameter of about 500 μm, a spheroid form of tonsil-derived mesenchymal stem cells (MSCs) have a diameter of about 250 μm as a self-assembly thereof is progressed right after the same is transferred into the microwell, wherein a cell aggregate with a relatively smooth appearance is formed when a culture is progressed, and then a cell aggregate with a diameter of 150 μm is produced when completely formed.

For example, in case of producing a cell aggregate by using a microwell with an average diameter of about 300 μm, a spheroid form of tonsil-derived mesenchymal stem cells (MSCs) have a diameter of about 100 μm as a self-assembly thereof is progressed right after the same is transferred into the microwell, wherein a cell aggregate with a relatively smooth appearance is formed when a culture is progressed, and then a cell aggregate with a diameter of 80 μm is produced when completely formed.

The present invention also provides a method for producing a spheroid form of parathyroid cells from tonsil-derived stem cells, the method comprising:

(a) transferring a suspension of tonsil-derived stem cells into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension;

(b) producing a spheroid form of tonsil-derived stem cells by culturing the tonsil-derived stem cells prepared by the step (a) in the hemispherical microwell; and (c) adding activin A and sonic hedgehog into the spheroid form of tonsil-derived stem cells of the step (b), thereby differentiating the stem cells into parathyroid cells.

The method for producing a spheroid form of parathyroid cells from tonsil-derived stem cells according to the present invention allows the tonsil-derived stem cells produced in a spheroid form to be differentiated into parathyroid cells, such that a differentiation potency is remarkably increased, secretion of parathyroid hormone is greatly increased, and a time for differentiating into parathyroid cells is much more reduced than an existing one. In other words, according to the present invention, a period of using a differentiation-inducing agent is remarkably reduced at a time of cell differentiation, and also a pre-differentiation period in a two-dimensional aspect is omitted, thereby achieving a remarkable effect as a differentiation method.

The contents mentioned in the method for producing a spheroid form of tonsil-derived stem cells can be appropriately modified in and applied to the steps (a) and (b).

The method for producing a spheroid form of parathyroid cells from tonsil-derived stem cells according to the present invention includes a step of adding activin A and sonic hedgehog to the spheroid form of tonsil-derived stem cells of the step (b) to be differentiated into parathyroid cells.

According to the method of the present invention, activin A, a component of a TGF-β super family, is a substance having an extensive biological activity such as mesoderm induction, nerve cell differentiation, bone remodeling and hematogenesis. According to the present invention, activin A may be contained at a concentration of 50 to 300 ng/ml, preferably 80 to 200 ng/ml.

Sonic hedgehog (shh), as one of three proteins in a mammalian signaling pathway family called hedgehog, is a kind of morphogen having different influences on embryo cells, which are under development depending on concentrations thereof, and also can control a cell division of adult stem cells. According to the present invention, sonic hedgehog may be contained at a concentration of 50 to 300 ng/ml, preferably 80 to 200 ng/ml.

According to the present invention, a step of being differentiated into parathyroid cells may be preferably performed for 3 to 15 days, more preferably for 4 to 10 days. These culture periods may be preferable, but can be also adjusted depending on a degree of differentiation into parathyroid cells, such that a desired spheroid form of cells can be produced. This step of differentiation enhances differentiation efficiency while remarkably shortening a differentiation period in comparison with an existing known two-dimensional culture method. According to an inventive method, medium used for inducing differentiation may be a conventional medium, which can be used for culturing stem cells, for example, DMEM (Dulbecco's modified Eagle medium), Keratinocyte-SFM (Keratinocyte serum free medium), RPMI-1640, etc, preferably DMEM medium.

A method for separating tonsil cells and a method for differentiating the same into parathyroid cells, used in the present invention, are respectively described in Korean Patent Registration Nos. 10-1508413 (a chimeric mesenchymal stem cell population and a method for producing the same) and 10-1520531 (a method for producing parathyroid hormone using tonsil stem cells); the contents of which are hereby incorporated by reference.

The present invention also provides a method for producing parathyroid hormone, the method comprising:

(a) transferring a suspension of tonsil-derived stem cells into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension;

(b) producing a spheroid form of tonsil-derived stem cells by culturing the tonsil-derived stem cells prepared by the step (a) in the hemispherical microwell;

(c) adding activin A and sonic hedgehog into the spheroid form of tonsil-derived stem cells of the step (b), thereby differentiating the stem cells into parathyroid cells; and (d) separating parathyroid hormone from culture medium or cell lysis solution obtained from the step (c).

The method for producing a spheroid form of parathyroid cells according to the present invention allows the tonsil-derived stem cells to be produced in a spheroid form and differentiated into parathyroid cells, such that a differentiation potency is remarkably increased, secretion of parathyroid hormone is greatly increased, and a time for differentiating into parathyroid cells is much more reduced than an existing one. In other words, according to the present invention, a period of using a differentiation-inducing agent is remarkably reduced at a time of cell differentiation, and also a pre-differentiation period in a two-dimensional aspect is omitted, thereby achieving a remarkable effect as a differentiation method.

The method for producing parathyroid hormone according to the present invention allows parathyroid hormone to be produced from a spheroid form of parathyroid cells with an enhanced secretory capacity, such that an amount of parathyroid hormone production is greatly increased in comparison with an existing known one and a time for cell differentiation is reduced, thereby achieving a remarkable effect on production of the parathyroid hormone.

The above-mentioned contents in the method for producing parathyroid cells can be modified in and applied to the steps (a), (b) and (c).

The method for producing parathyroid hormone according to the present invention comprises: separating parathyroid hormone from a cell lysis solution or culture medium obtained from the step (d).

The step of separating parathyroid hormone from a cell lysis solution or culture medium may be performed by using a general method, which can be used for separating and refining a protein. For example, methods such as affinity chromatography, ion-exchange chromatography, codeposition, etc., can be used, but not limited thereto and can be also appropriately selected and performed by an artisan of ordinary skill.

The parathyroid hormone is produced within a parathyroid cell, after which the parathyroid hormone is present within the cell as a secretory granule form and it is determined whether the parathyroid hormone is secreted out of the cell or not depending on exocellular calcium concentrations. Therefore, in order to facilitate a separation of the parathyroid hormone by promoting an exocellular secretion of the same produced from a parathyroid tissue cell induced from tonsil stem cells, this inventive method may further comprise: secreting parathyroid hormone out of a cell by adjusting a calcium concentration of culture medium after the step (c).

Preferably, in order to promote a secretion of the parathyroid hormone from the parathyroid cell, a calcium concentration of culture medium may by less than 1.5 mM, preferably less than 1.0 mM, more preferably less than 0.5 mM and most preferably less than 0.1 mM.

The present invention also provides a method for producing a spheroid form of parathyroid cells, the method comprising:

(a) treating tonsil-derived stem cells with activin A and sonic hedgehog to differentiate the tonsil-derived stem cells;

(b) transferring a suspension of cells of the step (a) into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension; and (c) adding activin A and sonic a hedgehog into the suspension of cells of the step (b) to differentiate the cells into a spheroid form of parathyroid cells.

The method for producing a spheroid form of parathyroid cells according to the present invention allows cells, which have been treated with pre-differentiation under the condition of a two-dimensional differentiation, to be cultured as a spheroid form on a three-dimensional condition, such that a differentiation potency thereof into parathyroid cells is remarkably increased, a secretion of parathyroid hormone is greatly increased, and a time for differentiation into parathyroid cells is much more reduced than an existing one.

The method for producing a spheroid form of parathyroid cells comprises: (a) treating tonsil-derived stem cells with activin A and sonic hedgehog to differentiate the tonsil-derived stem cells.

According to the present invention, activin A may be contained at a concentration of 50 to 300 ng/ml, preferably 80 to 200 ng/ml. According to the present invention, sonic hedgehog (shh) may be contained at a concentration of 50 to 300 ng/ml, preferably 80 to 200 ng/ml.

According to the present invention, in a step of being differentiated into parathyroid cells, a culture period can be adjusted depending on a method and period for being differentiated into a spheroid form of cells, preferably for 1 to 20 days in a two-dimensional aspect. According to an inventive method, medium used for inducing differentiation may be conventional ones, which can be used for culturing stem cells, for example, DMEM (Dulbecco's modified Eagle medium), Keratinocyte-SFM (Keratinocyte serum free medium), RPMI-1640, etc., preferably DMEM.

In case of the steps (b) and (c), the steps (a) and (c) of the above-mentioned method for producing a spheroid form of parathyroid cells from tonsil-derived stem cells can be also applied to this method for producing a spheroid form of parathyroid cells within a scope of proper decision made by those skilled in the art.

The present invention also provides a method for producing parathyroid hormone, the method comprising:

(a) treating tonsil-derived stem cells with activin A and sonic hedgehog to differentiate the tonsil-derived stem cells;

(b) transferring a suspension of cells of the step (a) into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension;

(c) adding activin A and sonic a hedgehog into the suspension of cells of the step (b) to differentiate the cells into a spheroid form of parathyroid cells; and (d) separating parathyroid hormone from culture medium or cell lysis solution obtained from the step (c).

The method for producing parathyroid hormone according to the present invention allows parathyroid hormone to be produced from a spheroid form of parathyroid cells with an enhanced secretory capacity, such that an amount of parathyroid hormone production is greatly increased in comparison with an existing known one, and a time for cell differentiation is reduced, thereby achieving a remarkable effect on production of the parathyroid hormone.

The steps (a), (b) and (c) are such as that mentioned in the above-mentioned method for producing a spheroid form of parathyroid cells. Furthermore, the contents of the step (d) described in the above-mentioned method for producing parathyroid hormone can be applied to the step (d).

The present invention also provides a spheroid form of tonsil-derived stem cells produced by the method for the producing a spheroid form of tonsil-derived stem cells. The spheroid form of tonsil-derived stem cells according to the present invention has advantages that a proliferation rate of stem cells per se is increased and differentiation potency into various cells such as parathyroid cells is remarkably increased.

The present invention also provides a spheroid form of parathyroid cells produced by the method for producing a spheroid form of parathyroid cells.

According to the present invention, a spheroid form of parathyroid cells shows a remarkable increase in production of parathyroid hormone as well as a great increase in expression of genes specific to a parathyroid tissue, such as GCM2 (glial cells missing homolog2), CaSR (calcium sensing receptor), CCL21 (chemokine(C-C motif) ligand 21) and CHGA (chromogranin A) in comparison with parathyroid cells produced by means of a general two-dimensional culture. Accordingly, the inventive cells achieve a remarkable effect as a product for parathyroid hormone production and cell therapy.

The present invention also provides a pharmaceutical composition for preventing or treating hypoparathyroidism or osteoporosis, containing a spheroid form of parathyroid cells produced by the method for producing a spheroid form of parathyroid cells.

In other words, the pharmaceutical composition can be used as a medicine for treating, diagnosing and preventing hypoparathyroidism and osteoporosis by using cells and tissues produced by means of separation from individuals, culture and special manipulation.

The composition for preventing or treating hypoparathyroidism and osteoporosis can be administered to patients, in such a way that the composition is formed into a pharmaceutical preparation of a unit dosage form suitable for administration to a patient's body, and the preparation contains an effective dosage for a single or several administrations. A formulation suitable for such purpose may be preferably a parenteral preparation such as a syringe and injection. Also, the composition for preventing or treating hypoparathyroidism and osteoporosis may contain a pharmaceutical acceptable conventional inactive carrier. Furthermore, the composition can be transplanted and administered to a patient by means of an administration method conventionally used in the art, preferably being directly engrafted or transplanted to the patient's troubled region, which requires a treatment, but not limited thereto. Also, in case of the administration, both a non-invasive method with a catheter and a surgical method such as injection or transplantation after incision of a troubled region are available. A dosage may be $1.0 \times 10^4$ to $1.0 \times 10^{10}$ cells/kg weight, preferably $1.0 \times 10^5$ to $1.0 \times 10^9$ cells/kg weight at once or several times. However, it should be understood that an actual dosage of effective components is decided considering various related factors such as a disease to be treated, a severity of disease, an administration route, a patient's weight, age and gender. Therefore, the dosage does not limit a scope of the present invention in any aspect.

Advantageous Effects of the Invention

A method for producing a spheroid form of tonsil-derived stem cells according to the present invention allows tonsil-derived stem cells to be cultured in a form of spheroid to thereby enhance a proliferation rate of the stem cells per se, and allows the same to increase a differentiation potency into parathyroid cells to thereby achieve a remarkable effect on growth of the tonsil-derived stem cells and differentiation of the same into parathyroid cells, etc.

DETAILED DESCRIPTION OF THE INVENTION

Hereinafter, embodiments and manufacturing examples will be suggested for better understanding of the present invention. However, the following examples and manufacturing examples are provided only for the purpose of illustrating the present invention, and thus the present invention is not limited thereto.

Example 1

Culture of Tonsil-Derived Stem Cells

Tonsillectomy was performed on six patients aged less than ten (five boys and one girl with an average age of 7.2 years) out of those who are patients in the department of otolaryngology head & neck surgery of Ewha Womans Univ. Mokdong Hospital. This study has passed a review of the Clinical Ethics Committee (ECT 11-53-02). Two thirds of enucleated tonsil tissues were used for a clinical biopsy, while the remaining one thirds of enucleated tonsil tissues was used for this experiment.

A collected tonsil tissue was washed in physiological saline water, after which a connective tissue within the tonsil tissue was comminuted in a cell culture medium RPMI-1640 (Roswell Park Memorial Institute medium 1640, Invitrogen Corporation, Carlsbad, Calif.), in which a collagenase type I (Invitrogen) of 210 U/ml of an enzyme-mixed solution is mixed with 10 µg/ml of DNAse (Sigma-Aldrich, St. Louise, Mo.), under the condition of 37° C. for 30 minutes. A suspended tissue was centrifuged and filtered out to obtain cells. The obtained cells were washed twice in RPMI 1640/20% NHS (normal human serum) (PAA Laboratories, GmbH, Paching, Austria) and once with RPMI 1640/10% NHS. The washed cells were applied to gradient centrifugation using Ficoll-Paque (GE Healthcare, Little Chalfont, Buckinghamshire, UK), such that mononuclear cells were obtained. The $10^8$ mononuclear cells were inoculated into DMEM-HG (Dulbecco's modified Eagle's medium-High Glucose) (Invitrogen) medium containing 10% FBS (Invitrogen), 100 µg/ml of streptomycin and 100 U/ml of ampicillin, and cultured for 48 hours. After culture, non-attached cells were removed while attached cells, considered as tonsil-derived mesenchymal stem cells (T-MSC), were subcultured up to three to five generations for four weeks, such that resulting cells were used in this experiment.

Example 2

Three-Dimensional Spheroid Culture of Tonsil-Derived Mesenchymal Stem Cells (TMSC) Using Concave Mold A method for three-dimensional culture of tonsil-derived stem cells obtained from the Example 1, was performed in a mold having a structure of FIG. 1. The mold used for inducing cells to form a three-dimensional spheroid structure is one which includes a microwell with 500 µm width and a depth of 300 µm and has a concave structure manufactured from polydimethylsiloxane (PDMS). This mold is one having a microwell width and depth optimal to the cell growth by forming a cell aggregate with a spheroid form structure, and has a merit that hundreds to thousands of spheroid-formed cells can be produced, if the mold is formed as a multiple-concave one.

Specifically, as described in Korean Patent Registration No. 10-1282926, this mold was manufactured in such a way that wells could be arranged at a density of 100 wells per a unit $cm^2$ by using soft lithography techniques and a meniscus of a polydimethysiloxane (PDMS) prepolymer, and then was used in an experiment after being coated with 3% (w/v) bovine serum albumin (BSA) in order to prevent cell attachment.

Figure 2:
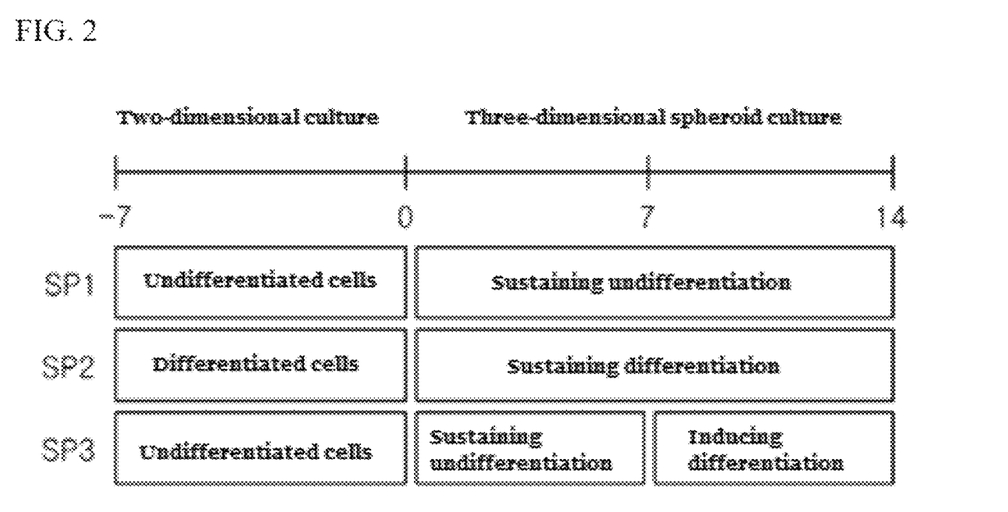
FIG. 2 depicts two- and three-dimensional culture process periods for producing a spheroid form of cells.

Using the concave mold, a spheroid form of cells were produced in such a way that tonsil-derived stem cells in a undifferentiated state or parathyroid cells differentiated from tonsil-derived stem cells were classified into the followings three types on the same condition as described in FIG. 2.

A first spheroid form of cells (SP1) was produced in such a way that cells in an undifferentiated state were cultured in a two-dimensional state for seven days under the condition of culturing tonsil-derived stem cells in the Example 1, after which the cells were removed with trypsin, transferred into a concave mold for inducing cells in a three-dimensional spheroid form, and further cultured for 14 days.

A second spheroid form of cells (SP2) was produced in such a way that tonsil-derived stem cells were cultured in a two-dimensional state for seven days in DMEM medium containing 5% FBS, activin A (100 ng/ml, R&D System, Inc. Minneapolis) and sonic hedgehog (Shh, 100 ng/ml, R&D Systems), so as to induce a differentiation thereof into parathyroid cells, after which the tonsil-derived cells were removed with trypsin, transferred into a concave mold for inducing cells in a three-dimensional spheroid formulation, and further cultured for 14 days.

A third spheroid form of cells (SP3) was produced in such a way that tonsil-derived stem cells were cultured in a two-dimensional state for seven days under the condition of culturing tonsil-derived stem cells in the Example 1, after which the tonsil-derived stem cells were removed with trypsin, transferred into a concave mold for producing the cells in a three-dimensional spheroid formulation, cultured for seven days under the condition of same medium without differentiation condition, so as to induce the cells to have a preferred orientation in the process of forming a spheroid form. After checking the spheroid shape has been formed, they were cultured for additional seven days in DMEM differentiation medium containing 5% FBS, activin A (100 ng/ml, R&D System, Inc. Minneapolis) and sonic hedgehog (Shh, 100 ng/ml, R&D Systems), which is differentiation medium.

In a process of producing a spheroid form of cells, $1 \times 10^3$ cells were seeded in one concave well, and undifferentiation or differentiation culture medium was replaced with new one every 2 to 3 days.

Example 3

Observation of Changes of a Shape, Size and Survival Rate of a Spheroid Form of Cells A shape and size of a spheroid form of cells, produced in the three types of SP1, SP2 and SP3, were observed with a microscope for appropriate culture period, and a size of each spheroid form of cells was measured in contrast by means of a scale bar in microscopy.

Also, in order to determining there is any change in cell survival, a survival state of the spheroid form of cells produced in three types of SP1, SP2 and SP3 was observed. Using LIVE/DEADassays kit (Invitrogen), live cells (green) and dead cells (red) during a process of producing spheroids were observed. This is based on a principle of promptly distinguishing between dead and live cells by simultaneously carrying out a green-fluorescent calcein-AM stain that reflects an presence of an intercellular esterase activity in live cells as well as a red-fluorescent ethidium homodimer-1 stain that indicates a loss of integrity of a plasma membrane, sensed from dead cells.

Figure 3:
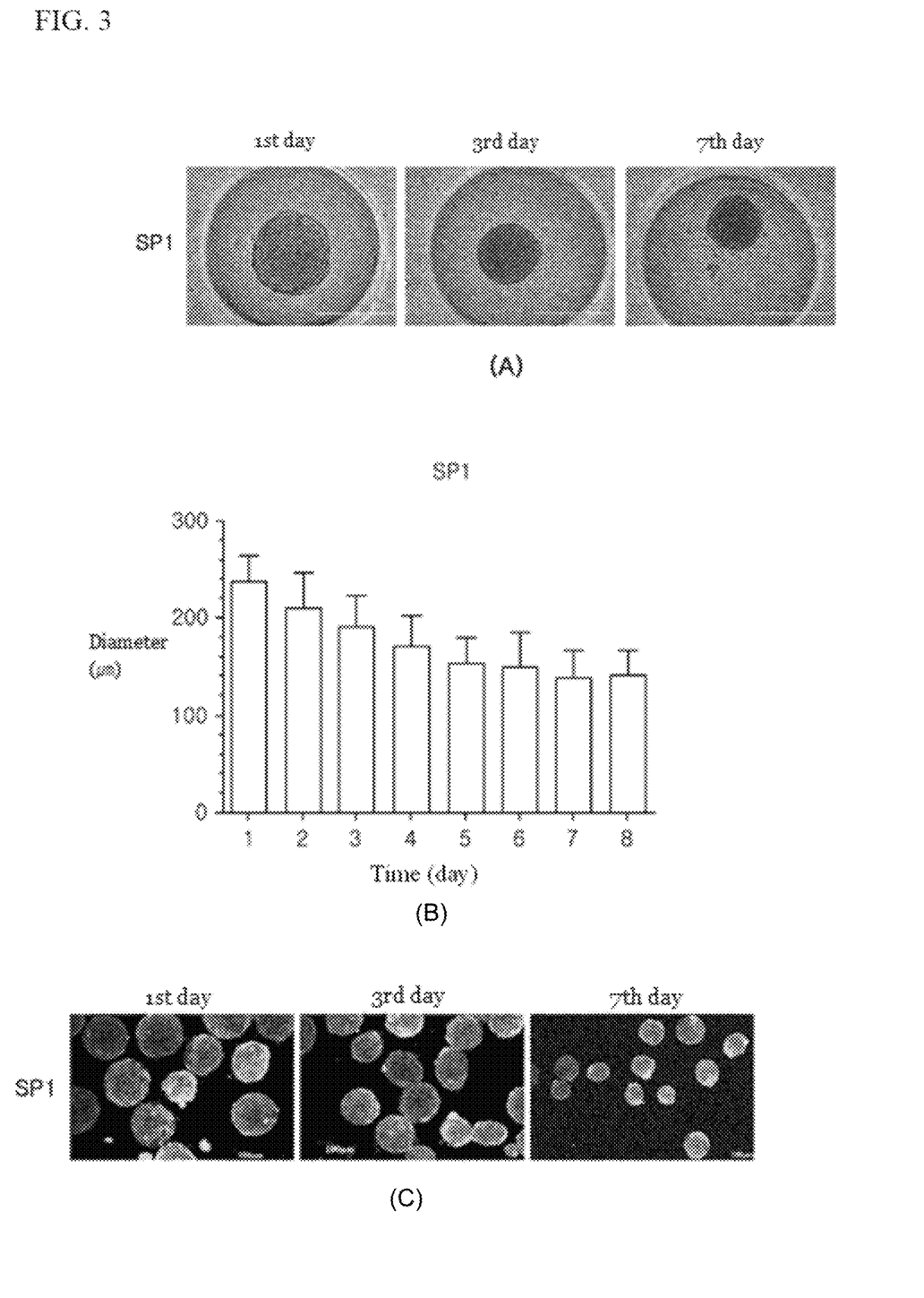
FIG. 3 depicts results of observing changes in a shape, size and survival of SP1 spheroid form of cells during producing the same.
Figure 4:
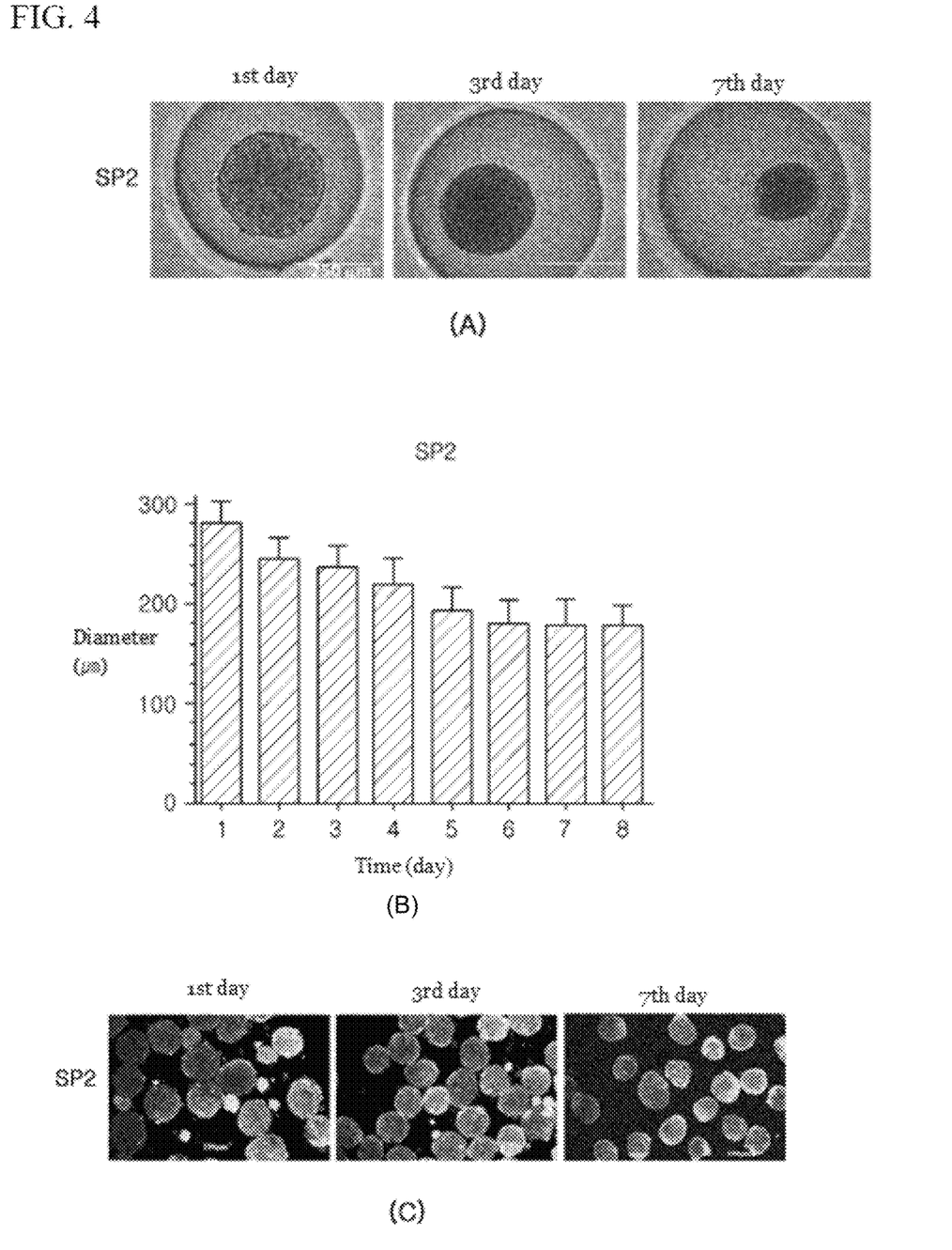
FIG. 4 depicts results of observing changes in a shape, size and survival of an SP2 spheroid form of cells during producing the same.
Figure 5:
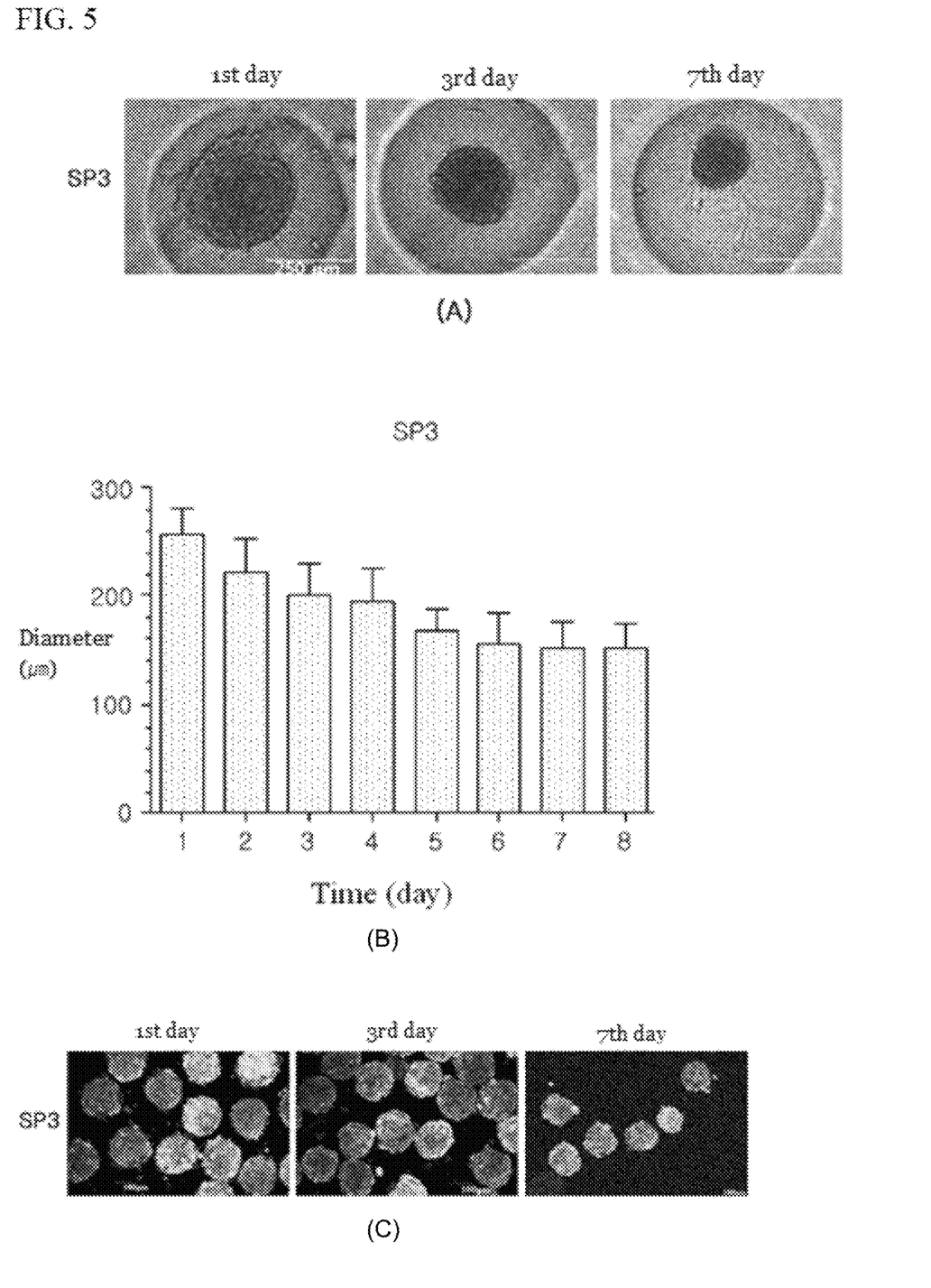
FIG. 5 depicts results of observing changes in a shape, size and survival of an SP3 spheroid form of cells during producing the same.

Results of the above-mentioned experiment were shown in FIGS. 3 to 5.

FIG. 3 shows results of experimenting on an SP1 spheroid form of cells, FIG. 4 does an SP2 spheroid form of cells and FIG. 5 does an SP3 spheroid form of cells.

FIG. 3 indicates results of experimenting on the SP1 spheroid form of cells.

FIG. 3A indicates a shape of a spheroid form of cells on first, third and seventh days during a process of culturing, while FIG. 3B does a size of cells. It was identified that the SP1 spheroid form of cells formed a spheroid sized at 237.44 μm at first and a small and condensed spheroid form of cells sized at 138.17 μm were produced on a seventh day. Also, FIG. 3C shows changes in a survival rate during a process of producing a spheroid form of cells. As shown in FIG. 3C, there was a very high frequency of green-stained live cells until a seventh day, while there were few red-stained dead cells until that day.

FIG. 4 shows results of experimentation on SP2 spheroid form of cells.

Changes in an SP2 spheroid shape were such as that shown in FIG. 4A, while changes in a size thereof were shown in FIG. 4B. It was identified that the SP2 formed a spheroid sized at 278.88 μm, somewhat larger than the SP1 at first, after which a size thereof was reduced gradually down to 177.88 μm on a seventh day. In other words, it was identified that the SP2 formed a larger and less-condensed spheroid shape than the SP1. Furthermore, unlike the SP1, it was identified that the SP2 showed a phenomenon, in which cells present within a spheroid spread out around the spheroid of the SP2, suggesting that this phenomenon is highly associated with an in vivo engraftment of the SP2 spheroid form of cells. FIG. 4C showed a viability of the SP2 spheroid form of cells, thus identifying that the SP2 showed a high survival rate of sustaining most live cells stained in green even until a seventh day.

FIG. 5 shows results of experimenting on an SP3 spheroid form of cells.

Changes in a shape of the SP3 spheroid were such as that shown in FIG. 5A, while changes in a size thereof were such as that shown in FIG. 5B. On a first day, a size of cells was 255.78 μm, in a middle between SP1 and SP2 spheroids. After period of spheroid forming, cells was condensed in size of 152.89 μm on a seventh day. A movement phenomenon, in which cells spread out around the SP3 spheroid, was identified more frequently than the SP2. FIG. 5C indicates viability of SP3 tonsil-derived stem cells, and it was identified that the cells showed a high survival rate even until a seventh day of culture.

Example 4

Observation of Differentiation of a Spheroid Form of Tonsil-Derived Stem Cells into Parathyroid Cells After producing a spheroid form cells, gene expression level of parathyroid hormone (PTH) was observed in which tonsil-derived stem cell group and differentiated parathyroid cell group with two-dimensional culture without spheroid formation was used as a control.

Using a trizol reagent, total RNA in cells were extracted and then gene expression pattern was measured by real time PCR (quantitative real time polymerase chain reaction, qRT-PCR) method using primers for a human parathyroid hormone gene. At the same time, glyceraldehyde-3-phosphate (GAPDH) was used as a control and its primers are as follows:

```
Parathyroid Hormone
Forward:
                                    (SEQ ID NO: 1)
5'-GAG TAG AAT GGC TGC GTA AGA AG-3'

Reverse:
                                    (SEQ ID NO: 2)
5'-TTC ATG GCT CTC AAC CAA GAC-3'

GAPDH
Forward:
                                    (SEQ ID NO: 3)
5'-GGA GCG AGA TCC CTC CAA AAT-3'

Reverse:
                                    (SEQ ID NO: 4)
5'-GGC TGT TGT CAT ACT TCT CAT GG-3'
```

Figure 6:
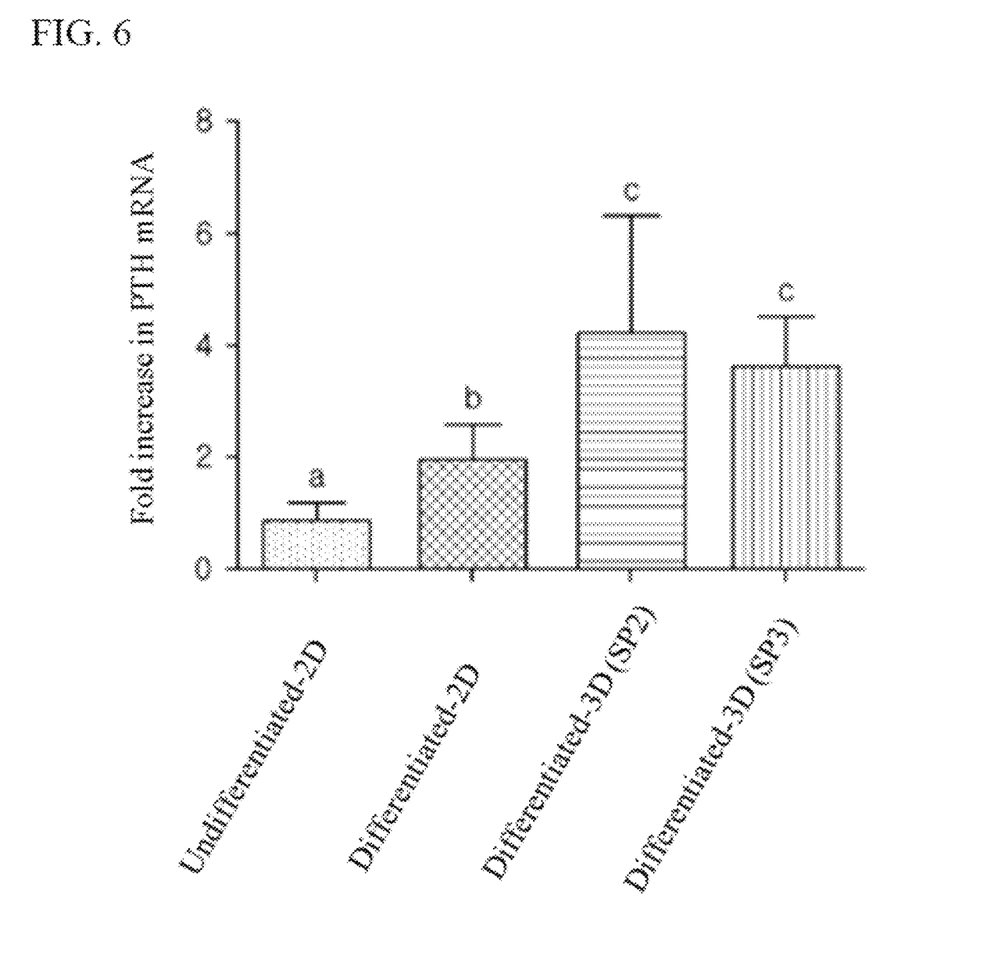
FIG. 6 depicts results of observing changes in a gene expression levels of parathyroid hormone from tonsil-derived stem cells and differentiated cells therefrom via two-dimensional culture and three-dimensional culture of spheroid forms.

Results of the above experiment were shown in FIG. 6.

As shown in FIG. 6, as a result of determining expression level of parathyroid hormone compared to an expression level of parathyroid hormone in undifferentiated tonsil-derived stem cells, an experiment group of tonsil-derived stem cells differentiated in a two-dimensional culture, an SP2 group and an SP3 group showed mRNA expression levels which were increased respectively by 2.3, 5.2 and 4.3 times more than an expression of parathyroid hormone in undifferentiated tonsil-derived stem cells. In particular, it was also identified that the SP2 and the SP3 showed mRNA expression levels, which were increased respectively by 2.2 and 1.9 times more than even an expression level of cells differentiated in a two-dimensional culture. In other words, it was identified that a culture into a spheroid form has a remarkable effect in comparison with the two-dimensional culture in terms of differentiation efficiency.

Based on the results, it was concluded that an expression of parathyroid hormone genes was induced more effectively in the three-dimensional culture method than in the two-dimensional culture one. Accordingly, it was suggested that a culture method under the condition of a microwell of a concave structure, which is formed in such a way that a liquid polymer is hardened, might be used as a physical culture environment in inducing an effect on expression of an identical gene, such that a period of using a differentiation inducing agent can be remarkably reduced, a period of pre-differentiation in a two-dimensional aspect can be further unnecessary, and a method for inducing expression and secretion of parathyroid hormone can be efficiently simplified.

Example 5

Observation of Differentiation of a Spheroid Form of Tonsil-Derived Stem Cells into Parathyroid Cells After a spheroid was completely formed for each culture period during a process of forming the spheroid form of cells SP1, SP2 and SP3, it was investigated by means of a confocal laser scanning microscope (LSM-5 Pascal EXCITER, Carl Zeiss) whether parathyroid hormone (PTH) and a chromogranin A (CHGA), associated to secretion of the parathyroid hormone (PTH), are expressed or not in cells present on a surface of tonsil-derived stem cells produced in a spheroid form as well as inside the spheroid during a differentiation into a parathyroid tissue.

After a surface of the spheroid form of cells is completely formed, a surface of the spheroid form of cells was washed in PBS, after which the cells were fixed with a 10% formalin solution. In the fixed cells, non-specific proteins were inactivated with a 2% bovine serum albumin (BSA) solution, after which each cell was treated with the 2% BSA solution containing a first antibody (PTH, CHGA and Cyr61) and reacted at 37° C. for four hours. After the reaction with the first antibody, a non-reacted antibody was washed twice in PBS and then reacted at 37° C. for one hour with the 2% BSA solution containing a second antibody (mouse IgG-FITC, rabbit-IgC-Rhodamine, Invitrogen) having a fluorescence corresponding to the first antibody. At this time, a nucleus-specific DAPI (4',6-Diamidino-2-Phenylindole, Dihydrochloride) (Molecular Probes) stain was added therein, such that a nucleus in each cell was stained at the same time. After an end of reaction with the second antibody, the surface of the cell was washed twice again in PBS, after which a cover glass attached with cells was removed and put on a glass for a fluorescence microscope, and attached onto the glass with a mounting solution, such that an expression level of an antibody and a distribution thereof within the cell were investigated on the fluorescence microscope.

Figure 7:
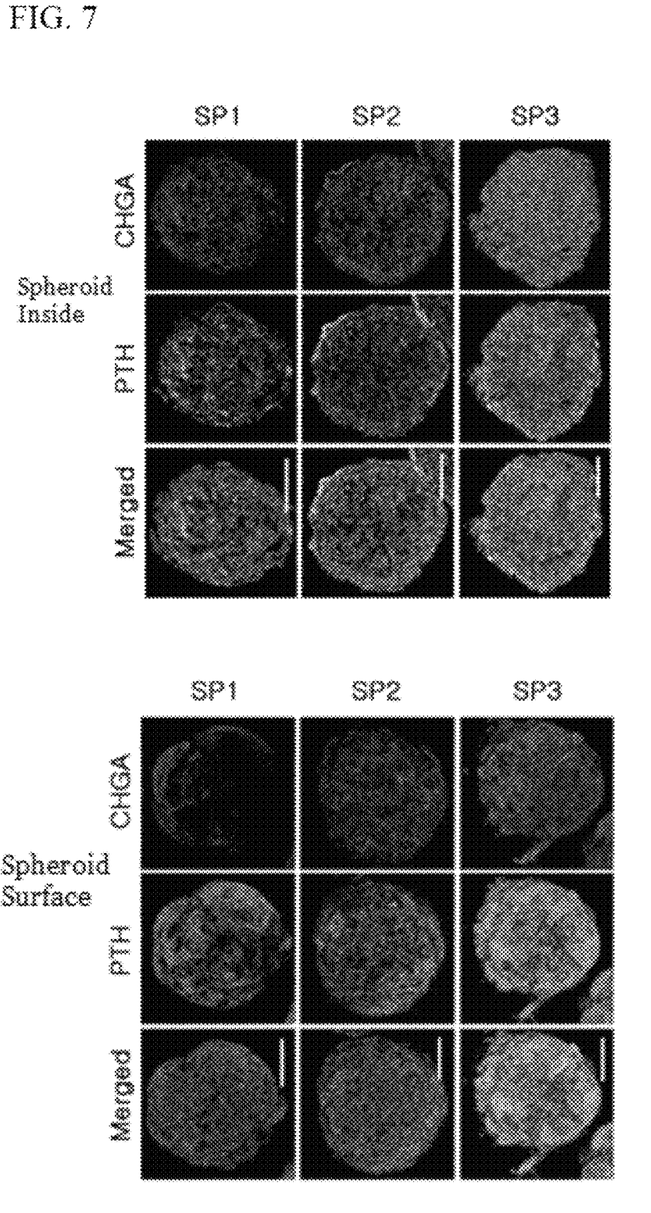
FIG. 7 depicts results of observing expression levels and distribution of parathyroid hormone (PTH) and a chromogranin A (CHGA) protein on a spheroid surface or inside of SP1, SP2 and SP3 spheroid forms of cells.
Figure 8:
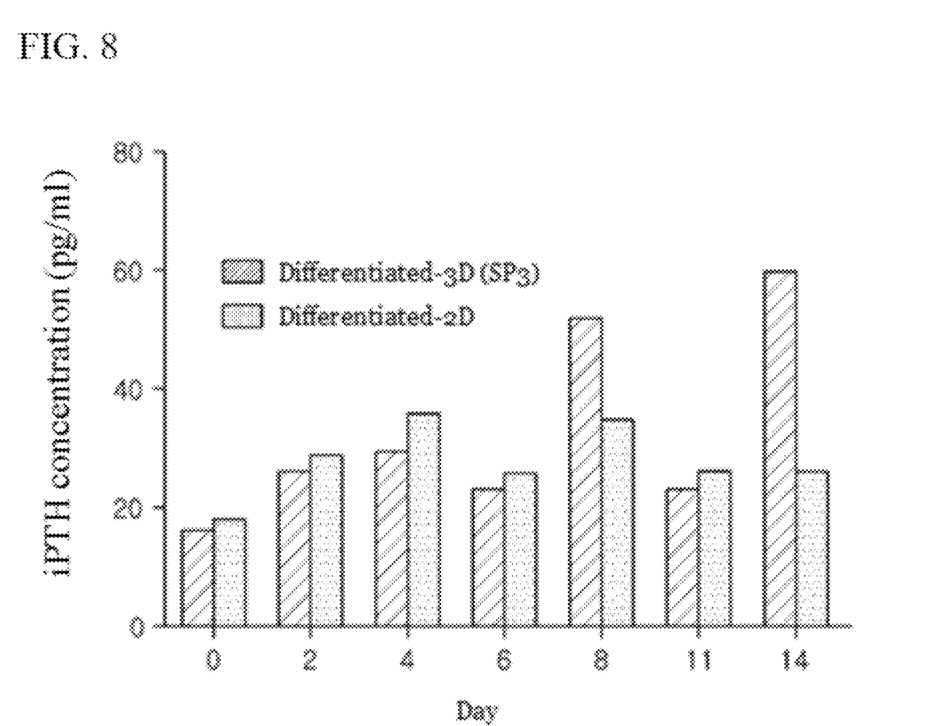
FIG. 8 depicts results of observing changes in a concentration of parathyroid hormone secreted from tonsil-derived stem cells and differentiated cells therefrom via two-dimensional culture and three-dimensional culture of spheroid forms.

Results were shown in FIG. 7.

As shown in FIG. 7, a presence of parathyroid hormone (PTH) produced in cells present on a surface and inside of a spheroid form of cells was identified by using three kinds of cells, which formed a spheroid form of cells. As a result of checking a presence of CHGA, a secretory granule protein of parathyroid hormone and the parathyroid hormone in SP1, SP2 and Sp3, by means of an immunostaining chemical method using an antibody specific to parathyroid hormone, SP1 did not show any remarkable distribution of expressions of PTH and CHGA on a surface or inside of the spheroid. On the other hand, it was concluded that the SP2 exhibited a significantly high expression both on a surface and inside of the spheroid than SP1. The SP3 indicated a remarkably high expression both on a surface and than SP2. Based on the experiment results, it was identified that the SP3 spheroid form of cells was the most advantageous culture condition in terms of PTH and CHGA expression. In particular, even if differentiation was induced just for seven days, it was identified that the SP3 showed a remarkable expression of PTH and CHGA. Such period was remarkably short in comparison with an existing known method, which took at least three weeks to induce differentiation.

Example 6

Observation of Differentiation of Spheroid Form of Tonsil-Derived Stem Cells into Parathyroid Cells During a process of forming a spheroid form of cells SP1, SP2 and SP3, whenever being replaced with a cell culture medium containing a differentiation inducing agent for each culture period, differentiated or undifferentiated media were collected to analyze a concentration of parathyroid hormone secreted outside cells. The cell culture medium collected for each period was filtered with a syringe filter of 0.45 μm, so as to remove cell floating matters, cell debris or the like, after which a filtered cell culture medium was freeze-dried and concentrated by using a freeze dryer (Operon).

A sample of a freeze-dried powder type was suspended again with phosphate buffered saline (pH 7.4), so as to investigate PTH concentration discharged by means of an electro-chemiluminescence immunoassay (ECLIA) method using avidity with an antibody to PTH protein.

Based on the above PTH concentration experiment, the results of a comparative experiment between SP3 and control group in which two-dimensional culture was performed with treatment of differentiation inducing agents.

It was concluded that the SP3 showed a remarkably higher PTH secretion concentration range of 18.0-35.6 pg/ml than a range of 16.1-59.8 pg/ml. In case of the SP3, even if an induced differentiation was performed just for seven days, the SP3 showed a remarkable PTH expression concentration, which was remarkably shortened in comparison with an existing known method, which took at least three weeks to induce differentiation, thereby exhibiting an effect of the present invention by showing a high level of PTH secretion.

Example 7

Observation of Differentiation of Spheroid Form of Tonsil-Derived Stem Cells into Parathyroid Cells Parathyroidectomized rats (PTX-rata), an animal model with a parathyroid resected, were used to investigate in vivo activity of a spheroid form of cells of SP3.

The PTX animal model was established in such a way that a rat was administered with 5-aminolevulinic acid hydrochloride (ALA) that is a fluorescent stain specific to parathyroid tissue, a neck region thereof was opened after two hours, and then parathyroid tissue was detected and surgically removed out.

An experimental animal group is one that an SP3 spheroid form of cells was administered into the PTX rat model, and was named PTX-SP3, out of which 10 animals were used.

An SP3 spheroid form of cells was percutaneously administered once by 1000 cells per rat, after which a survival of rats was checked and a behavioral ecology of rats was investigated periodically for three months. Out of a group of rats intraperitoneally administered with PTH drug at a normal physiological concentration (PTX-rhPTH) and normal rats without a surgery, ten animals were used respectively as a positive control group.

Figure 9:
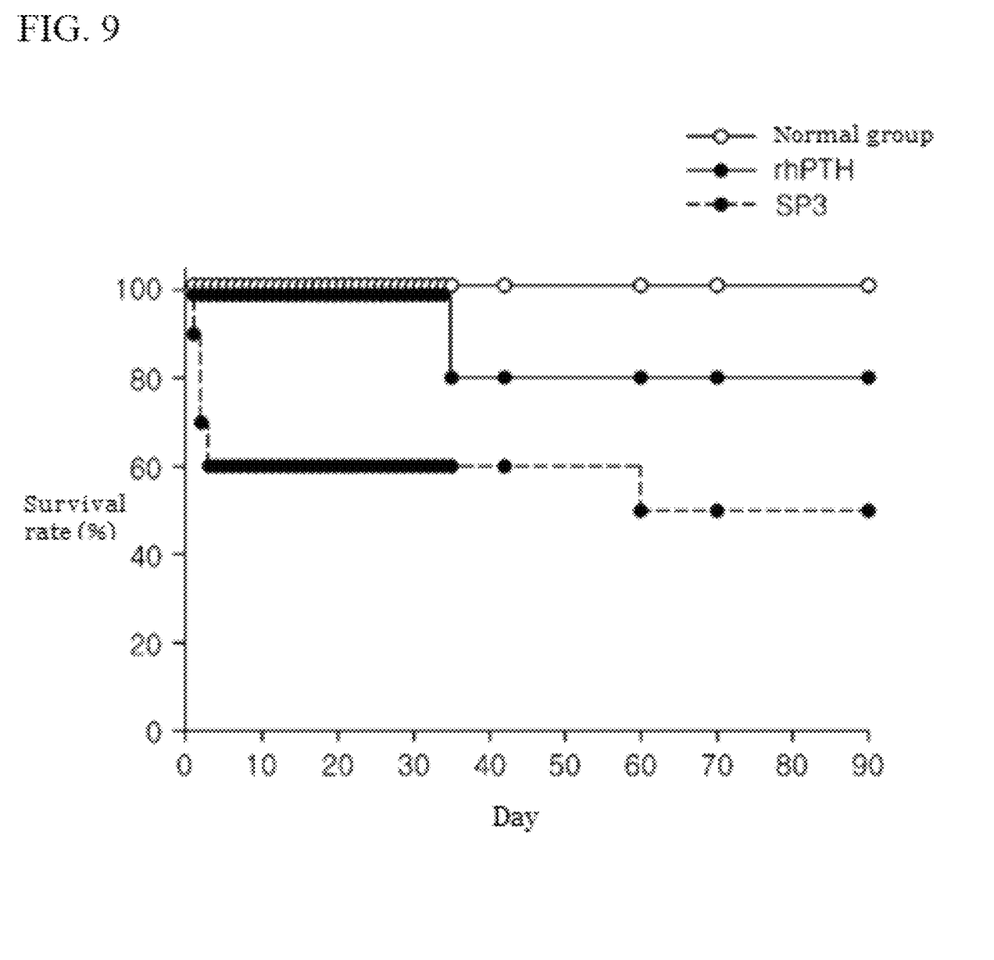
FIG. 9 depicts results of observing changes in survival rates of a spheroid form of cells-administered parathyroidectomized rats SP3 for 3 months.
Figure 10:
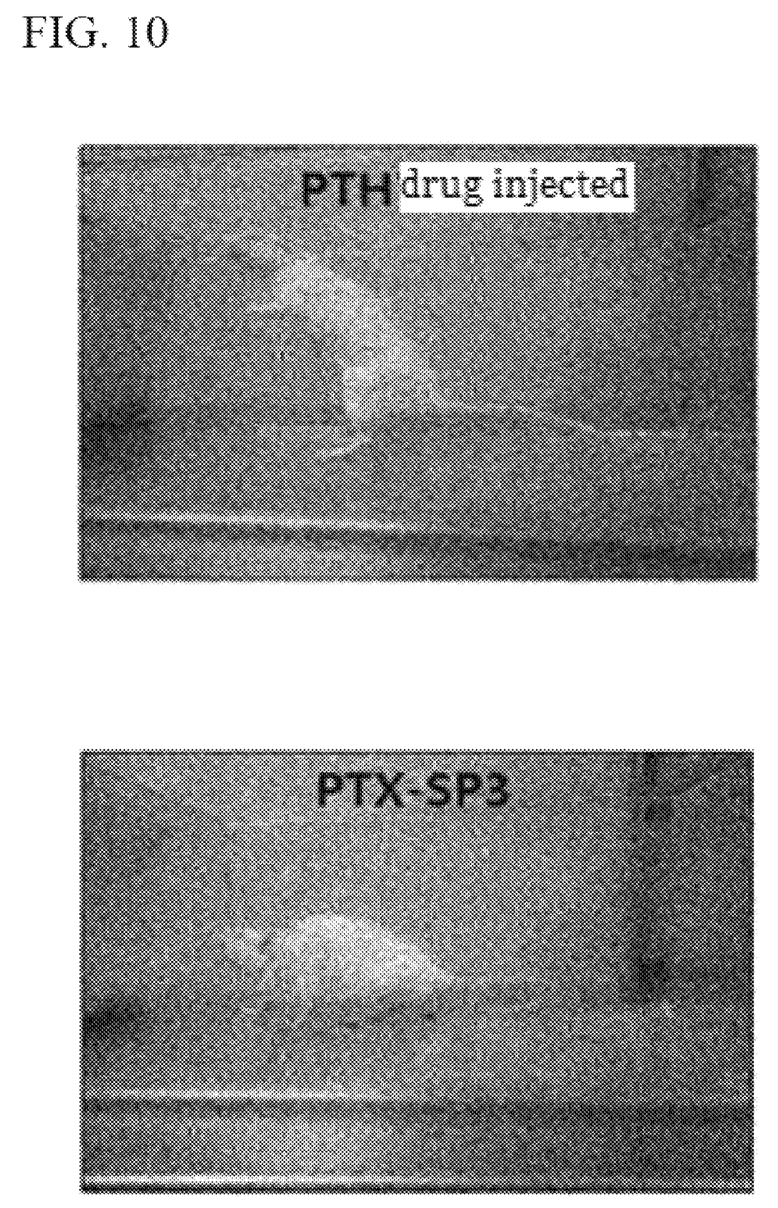
FIG. 10 depicts results of observing changes in a behavior and appearance of a spheroid form of cells-administered parathyroidectomized rats SP3 after 3 months.

Results of the experiment were shown in FIGS. 9 and 10.

FIG. 9 indicates changes in a survival rate in case of administration of a spheroid form of cells. As a result of the experiment, it was identified that a survival rate was increased upon an administration of a spheroid form of cells, though an effect thereof was somewhat less than PTH drug itself used as a positive control. In case of an experiment performed for 90 days, it was also identified that the SP3 showed a remarkable effect in a continuity aspect by maintaining an effect resulting from the administration of cells.

Also, behaviors and appearances of a rat percutaneously administered with spheroid were shown in FIG. 10. It was identified that the rat showed a similar degree of behaviors to the rat of the positive control group in behavioral aspects such as weight loss, fur shape and walking, while also achieving a similar degree of an effect to the positive control group in terms of weight changes.

The invention claimed is:

1. A method for producing a spheroid form of parathyroid cells from tonsil-derived stem cells, the method comprising:
   (a) transferring a suspension of undifferentiated tonsil-derived stem cells into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension;
   (b) producing a spheroid form of undifferentiated tonsil-derived stem cells by culturing the undifferentiated tonsil-derived stem cells prepared by the step (a) in the hemispherical microwell; and
   (c) adding activin A and sonic hedgehog into the spheroid form of undifferentiated tonsil-derived stem cells of the step (b), thereby differentiating the stem cells into parathyroid cells.

2. The method of claim 1, wherein the microwell is formed in such a way that polydimethylsiloxane is hardened.

3. The method of claim 1, wherein the culture of the step (b) is performed for 1 to 20 days.

4. The method of claim 3, wherein the culture of the step (b) is performed for 1 to 14 days.

5. The method of claim 1, wherein activin A is contained at a concentration of 50 to 300 ng/ml and sonic hedgehog is contained at a concentration of 50 to 300 ng/ml.

6. The method of claim 1, further comprising (d) separating the produced spheroid form of parathyroid cells, wherein the separated form of parathyroid cells is formulated as a pharmaceutical composition for treating hypoparathyroidism or osteoporosis.

7. The method of claim 6, wherein the pharmaceutical composition of the spheroid form of parathyroid cells is administered to subject with hypoparathyroidism or osteoporosis for treating hypoparathyroidism or osteoporosis.

8. The method of claim 1, wherein the parathyroid cell is capable of producing or secreting parathyroid hormone.

9. A method for producing parathyroid hormone from tonsil-derived stem cells, the method comprising:
   (a) transferring a suspension of undifferentiated tonsil-derived stem cells into a hemispherical microwell that is formed in such a way that at least one liquid polymer is hardened in a form of hemispherical microwell, wherein the liquid polymer is selected from among polydimethylsiloxane, silicon polymer, polybutadiene, polyisobutylene and polyurethane and forms a meniscus due to surface tension;
   (b) producing a spheroid form of undifferentiated tonsil-derived stem cells by culturing the undifferentiated tonsil-derived stem cells prepared by the step (a) in the hemispherical microwell containing a culture medium;
   (c) adding activin A and sonic hedgehog into the spheroid form of undifferentiated tonsil-derived stem cells of the step (b), thereby differentiating the stem cells into parathyroid cells; and
   (d) separating produced parathyroid hormone from the culture medium or a cell lysis solution.

10. The method of claim 9, the method further comprising: allowing parathyroid hormone to be secreted out of cells by adjusting a calcium concentration of the culture medium after the step (c).

11. The method of claim 9, wherein the culture is performed for 1 to 14 days.

* * * * *